(12) United States Patent
Olevsky et al.

(10) Patent No.: US 8,585,763 B2
(45) Date of Patent: Nov. 19, 2013

(54) SPRING DEVICE FOR LOCKING AN EXPANDABLE SUPPORT DEVICE

(75) Inventors: Boris Olevsky, Fair Lawn, NJ (US); Alla Olevsky, legal representative, Fair Lawn, NJ (US); Francesco A. Larosa, Neptune, NJ (US); Nelson Li, Hillsdale, NJ (US); E. Skott Greenhalgh, Lower Gwynedd, PA (US); John-Paul Romano, Chalfont, OR (US)

(73) Assignee: Blackstone Medical, Inc., Lewisville, TX (US)

( * ) Notice: Subject to any disclaimer, the term of this patent is extended or adjusted under 35 U.S.C. 154(b) by 125 days.

(21) Appl. No.: 13/174,701

(22) Filed: Jun. 30, 2011

(65) Prior Publication Data

US 2013/0006358 A1    Jan. 3, 2013

(51) Int. Cl.
 *A61F 2/44* (2006.01)
(52) U.S. Cl.
 USPC .................................. 623/17.16; 623/17.15
(58) Field of Classification Search
 CPC ..................................................... A61F 2/4455
 USPC ........................................ 623/17.15, 17.16
 See application file for complete search history.

(56) References Cited

U.S. PATENT DOCUMENTS

| | | | |
|---|---|---|---|
| 3,984,191 | A | 10/1976 | Doty |
| 5,611,639 | A | 3/1997 | Levenberg |
| 5,704,100 | A | 1/1998 | Swan |
| 6,176,881 | B1 | 1/2001 | Schar et al. |
| 6,644,884 | B2 | 11/2003 | Gledhill |
| 6,743,463 | B2 | 6/2004 | Weber et al. |
| 6,861,088 | B2 | 3/2005 | Weber et al. |
| 7,156,874 | B2 | 1/2007 | Paponneau et al. |
| 7,278,185 | B2 | 10/2007 | Smith |
| 7,455,875 | B2 | 11/2008 | Weber et al. |
| 7,588,573 | B2 | 9/2009 | Berry |
| 7,914,581 | B2 | 3/2011 | Dickson et al. |
| 8,252,054 | B2 | 8/2012 | Greenhalgh et al. |
| 2006/0004376 | A1 | 1/2006 | Shipp et al. |
| 2006/0004447 | A1 | 1/2006 | Mastrorio et al. |

(Continued)

FOREIGN PATENT DOCUMENTS

WO    03082363 A1    11/2003

OTHER PUBLICATIONS

International Search Report and Written Opinion; PCT/US2012/044959, dated Sep. 25, 2012, 7 pages.

(Continued)

*Primary Examiner* — Ellen C Hammond
(74) *Attorney, Agent, or Firm* — Baker & McKenzie LLP (57) ABSTRACT

A locking device for locking an expandable support device, where the locking device includes a spring device integral with the expandable support device, and the spring device includes an end portion, a first flexible arm, and a second flexible arm. A first aperture of the spring device is adapted to position the fastener associated with the first rotational position and a second aperture of the spring device is adapted to position the fastener associated with the second rotational position. The first flexible arm and second flexible arm are adapted to flex outward and allow passage of the fastener head when an inward pressure is applied to the fastener positioned in the second aperture. The first flexible arm and the second flexible arms are adapted to collapse to their unflexed position after the fastener head has completed passage through the spring device, such that the first flexible arm and the second flexible arm are adapted to cover the fastener head and prevent the fastener from backing out.

20 Claims, 7 Drawing Sheets

(56) References Cited

U.S. PATENT DOCUMENTS

| | | | |
|---|---|---|---|
| 2006/0069436 | A1 | 3/2006 | Sutton et al. |
| 2007/0191954 | A1 | 8/2007 | Hansell et al. |
| 2009/0138089 | A1 | 5/2009 | Doubler et al. |
| 2009/0204215 | A1 | 8/2009 | McClintock et al. |
| 2009/0281579 | A1 | 11/2009 | Weaver et al. |
| 2010/0145456 | A1 | 6/2010 | Simpson et al. |
| 2010/0179657 | A1 | 7/2010 | Greenhalgh et al. |
| 2010/0274357 | A1 | 10/2010 | Miller et al. |
| 2010/0298942 | A1 | 11/2010 | Hansell et al. |
| 2011/0112587 | A1 | 5/2011 | Patel et al. |
| 2011/0251692 | A1 | 10/2011 | McLaughlin et al. |

OTHER PUBLICATIONS

International Search Report and Written Opinion; PCT/US2012/044963, dated Sep. 25, 2012, 6 pages.

Walton, et al., "Inhibition of Prostaglandin E2 Synthesis in Abdominal Aortic Aneurysms: Implications for Smooth Muscle Cell Viability, Inflammatory Processes, and the Expansion of Abdominal Aortic Aneurysms," Circulation Jul. 6, 1999, pp. 48-54.

Tambiah, et al., "Provocation of experimental aortic inflammation and dilatation by inflammatory mediators and *Chlamydia pneumoniae*," British Journal of Surgery, 2001, 88, pp. 935-940.

Franklin, et al., "Uptake of tetracycline by aortic aneurysm wall and its effect on inflammation and proteolysis," British Journal of Surgery, 1999, 86, pp. 771-775.

Xu, et al., "Sp1 Increases Expression of Cyclooxygenase-2 in Hypoxic Vascular Endothelium: Implications for the Mechanisms of Aortic Aneurysm and Heart Failure," The Journal of Biological Chemistry, vol. 275, No. 32, Issue Aug. 11, 2000, pp. 24583-24589.

Pyo, et al., "Targeted gene disruption of matrix metalloproteinase-9 (gelatinase B) suppresses development of experimental abdominal aortic aneurysms," The Journal of Clinical Investigation, Jun. 2000, vol. 105, No. 11, pp. 1641-1649.

SPRING DEVICE FOR LOCKING AN EXPANDABLE SUPPORT DEVICE

TECHNICAL FIELD

The present disclosure relates in general to medical device technology, and more specifically to a spring device for locking an expandable (height adjustable) support device into proper expanded position.

BACKGROUND

Generally, an expandable vertebral body replacement device requires screws or other fasteners to achieve proper extension during vertebral body replacement. Additionally, certain vertebral body replacements may require screws or other fasteners to secure into position one or more components relative to one another. For example, certain expandable vertebral body replacements may have an outer cylinder that can be rotated about an interior extendable leg, such that the extended position is locked in place with a screw.

One of the problems with these techniques is the tendency of screws or other fasteners to work loose after fixation. Slight or extreme shock or vibration of the vertebrae, due to normal or rigorous activities of the patient, increases the risk that the screws may become loose or back out. If a screw becomes loose or unattached, the consequences can be significant for the health of a patient.

There remains a need for a locking device to not only lock a screw into a desired position, but also to prevent the screw from backing out. Further, there remains a need to achieve these goals without the need for auxiliary screws or separate components that may get lost in the patient's body. Thus, there is a need for an improved and simpler locking device that can be machined onto a component that will allow a screw to be locked into position and prevent the screw from backing out.

SUMMARY

In accordance with the present invention, a locking device for locking an expandable support device, where the locking device includes a spring device integral with the expandable support device, and the spring device includes an end portion, a first flexible arm, and a second flexible arm. The expandable support device includes a first member having an outer cylinder, where the outer cylinder includes a slot and a spring device. The expandable support device also includes a second member positioned concentrically inside of the first member, where the second member is configured to rotate with respect to the first member, and the second member includes a hole. The expandable support device also includes a fastener extending through the spring device, the slot of the first member, and the hole of the second member, where the fastener includes a head.

A first aperture of the spring device is adapted to position the fastener associated with the first rotational position and a second aperture of the spring device is adapted to position the fastener associated with the second rotational position. The first flexible arm and second flexible arm are adapted to flex outward and allow passage of the fastener head when an inward pressure is applied to the fastener positioned in the second aperture. The first flexible arm and the second flexible arms are adapted to collapse to their unflexed position after the fastener head has completed passage through the spring device, such that the first flexible arm and the second flexible arm are adapted to cover the fastener head and prevent the fastener from backing out.

The present disclosure provides several important technical advantages. In certain embodiments, the present disclosure provides mechanisms for locking in a position with a fastener and prevent the fastener from backing out. Further, this mechanism can be achieved with a single device machined onto a component. Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the features and advantages of the present disclosure, reference is now made to the detailed description along with the accompanying figures and in which.

DETAILED DESCRIPTION

While the making and using of various embodiments of the spring device according to the present disclosure are discussed in detail below, it should be appreciated that the present application provides many applicable inventive concepts that can be embodied in a wide variety of specific contexts. Without limiting the scope of the present disclosure, the spring device is described in connection with an expandable support device having an upper extension leg and a lower extension leg. However, the spring device can be used with other devices (e.g., expandable support devices which only has one extension leg, an interbody device having a flat or a curved surface, a cover plate, a cervical plate, etc.). The specific embodiments discussed herein are merely illustrative of specific ways to make and use the spring device disclosed herein and do not delimit the scope of the application, and their usage does not delimit the application, except as outlined in the claims.

Figure 1:
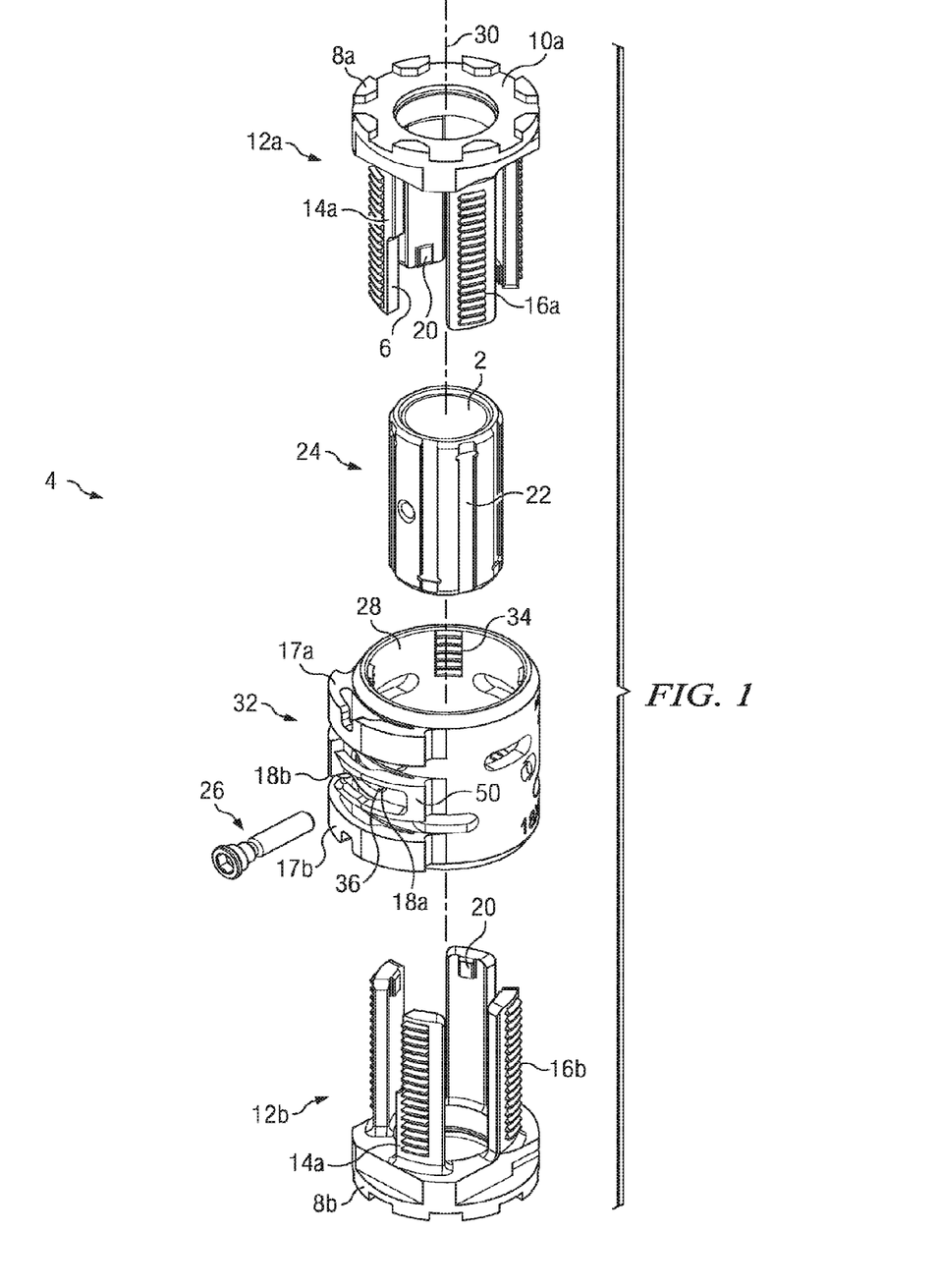
FIG. 1 is an exploded view of an expandable support device according to one embodiment of the present disclosure.
Figure 4A:
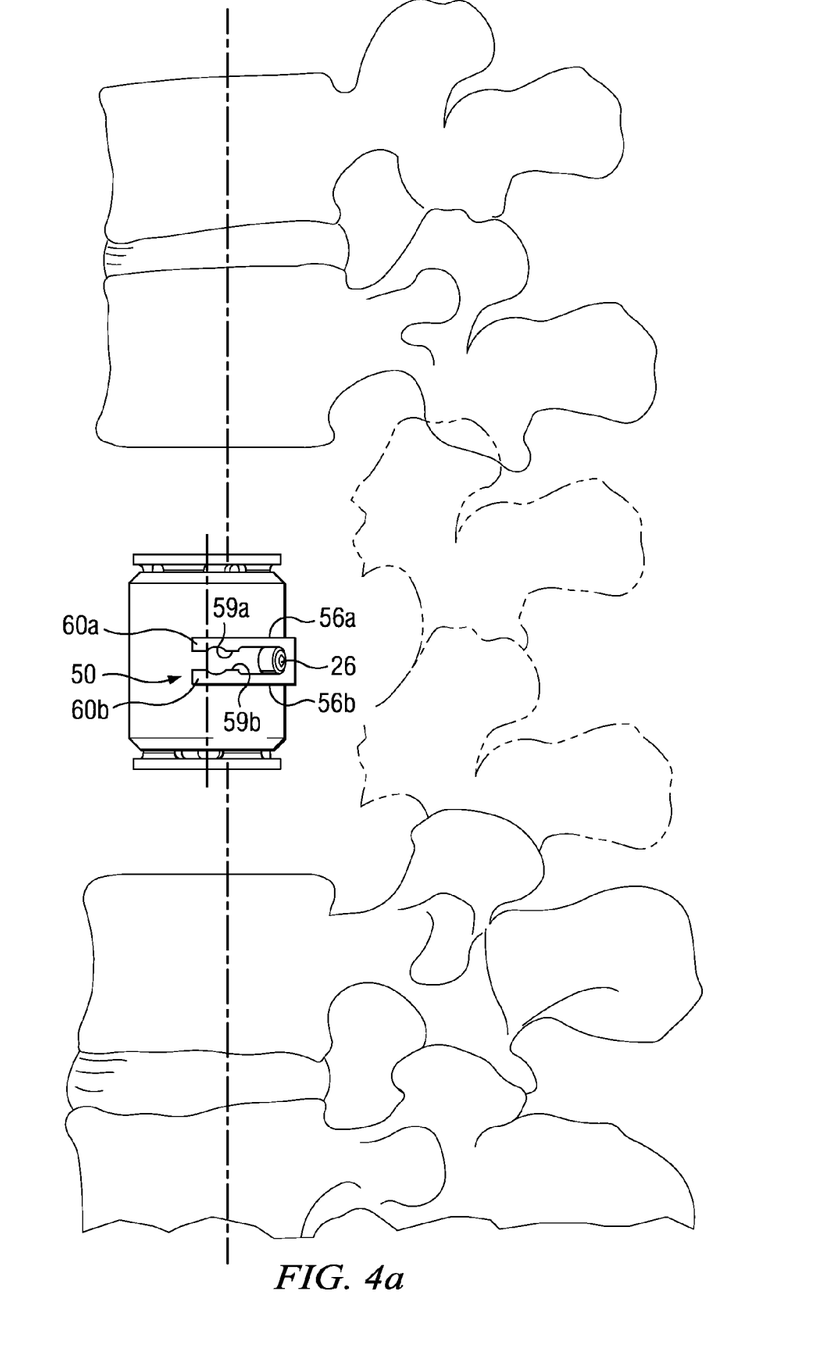
FIG. 4A is a lateral view of an expandable support device in its compressed configuration within vertebral bodies of a spine according to one embodiment of the present disclosure.
Figure 4B:
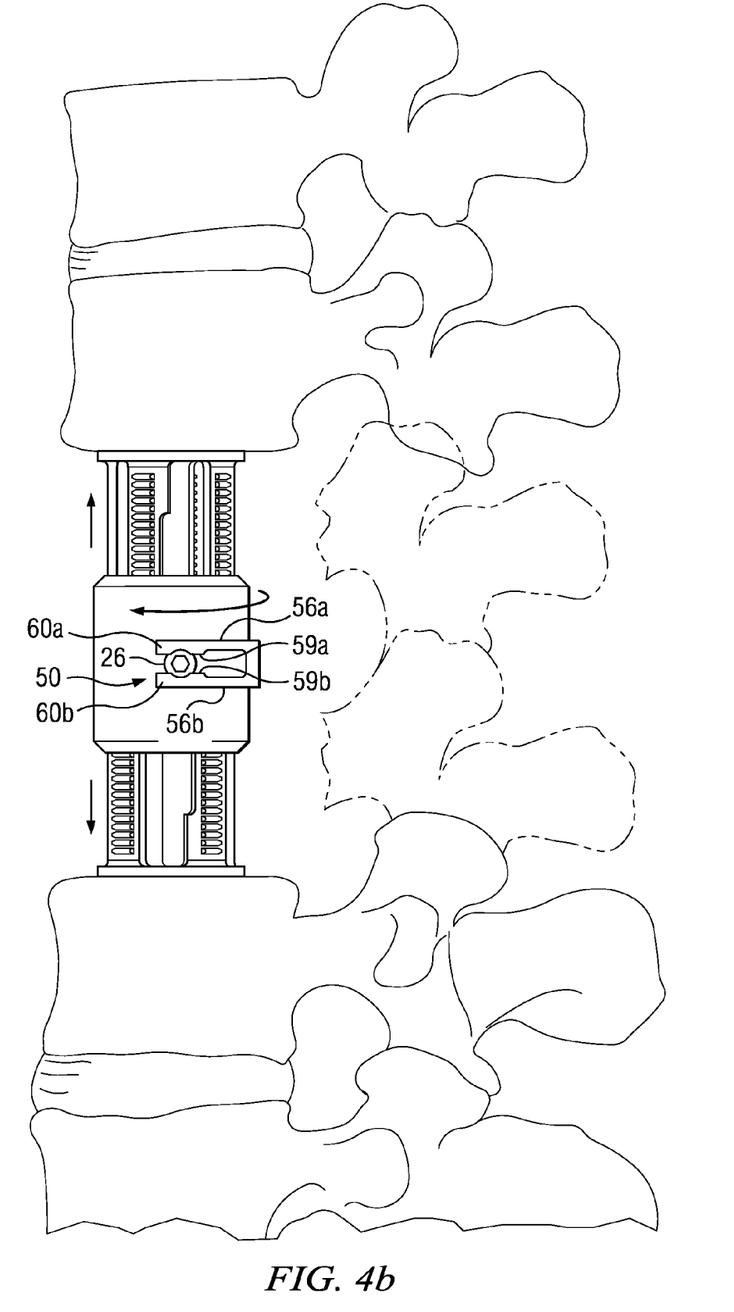
FIG. 4B is a lateral view of an expandable support device in its extracted and locked configuration within vertebral bodies of a spine according to one embodiment of the present disclosure.

FIG. 1 is an exploded view of an expandable support device 4 according to one embodiment of the present disclosure. One or more adjacent vertebral bodies 66, as illustrated in FIGS. 4A and 4B, and one or both surrounding vertebral discs—as well as the vertebral discs between the removed vertebral bodies 66—can be removed from a target site. The expandable support device 4 can then be inserted into the target site and expanded to provide mechanical support in the spine 62 between the remaining vertebral bodies 66. The embodiment of the expandable support device illustrated in FIG. 1 is described in U.S. application Ser. No. 12/684,825 to Greenhalgh et al. and is hereby incorporated by reference in its entirety. It should be appreciated that many features disclosed in this application, including, but not limited to spring device 50, are not taught, suggested, or disclosed in U.S. application Ser. No. 12/684,825.

The expandable support device 4 can have an outer cylinder 32, an inner cylinder 24, a first end piece 12a and a second end piece 12b. The expandable support device 4 can be expanded and can mechanically, structurally support orthopedic structures in vivo, whether those orthopedic structures are the aforementioned vertebrae 64, other bones, or soft tissue.

The first end piece 12a and second end piece 12b can be substantially identical or different from each other in shape and structure. The first end piece 12a can be symmetric or a mirror-image of the second end piece 12b. The first 12a and second 12b end pieces can have terminal first 8a and second 8b ends, respectively. The ends can have end faces. The end faces can be smooth or textured. The end faces can be textured with knurling, spikes, ridges, bumps, or combinations thereof. A first end face 10a can be textured with a first texture and the second end face 10b can be smooth or textured with a second texture that can be the same or different from the first texture. The end faces can be configured to abut or dig into adjacent tissue (e.g., bone) during implantation. Either or both end faces can be made from or lined with a matrix to encourage tissue ingrowth into the end face.

The end pieces can have one or more end piece extensions or legs extending from the respective end faces longitudinally inward toward the longitudinal center of the expandable support device 4. The extensions can have one or more radially outward-facing end piece teeth. The end piece teeth can be configured in a longitudinal column parallel with the longitudinal axis 30 on each extension. The end piece teeth can be oriented in transverse planes, perpendicular to the longitudinal axis 30 and along an angular path at a constant radius with respect to the longitudinal axis 30. Each end piece tooth can extend across half (as shown) or substantially all of the radially outer surface of the extension.

One, two or all of the extensions can have radially inwardly-facing guide pegs 20. The guide pegs 20 can be at or near the longitudinally terminal ends of the extensions away from the respective end face.

End piece slots 6 can be formed by open areas between the extensions.

The inner cylinder 24 can form a center channel 2. The inner cylinder 24 can have longitudinal guide slots 22 on the radially outer surface of the inner cylinder 24. The guide slots 22 can be configured to interface with, or receive, the guide pegs 20. The guide slots 22 can be configured to longitudinally slidably attach to the guide pegs 20. The guide slots 22 can constrain the guide pegs 20 to prevent the end pieces (and guide pegs 20) from rotating with respect to the inner cylinder 24.

During use, filler can be inserted through the end piece slots 6 and into the center channel 2 before during or after insertion of the device 4 into the target site and/or extension of the device 4. The filler can be chunks of morselized bone, powder (e.g., BMP), liquid (e.g., PMMA), all of which are listed and for which examples are given below, or combinations thereof.

The inner cylinder 24 can have one or more a radially outwardly extending lock screws 26. The lock screws 26 can have heads at the radially outermost terminal end of the lock screw 26. The heads of the lock screws 26 can be wider than the shafts of the lock screws 26. The lock screws 26 can be spring-loaded, clips, or combinations thereof. As used herein, screw 26 can refer to any suitable type of fastener with its head and body configured in any suitable way in use with the present application.

The outer radius of the inner cylinder 24 can be smaller than the inner radius of the end piece extensions.

The outer cylinder 32 can have a screw slot 36 configured to slideably receive the lock screw 26. The outer cylinder 32 can have an inner radius that is larger than the outer radius of the end piece extensions.

The screw slot 36 can have a first stop 18a at a first terminal end of the screw slot 36. The screw slot 36 can have a second stop 18b at a second terminal end of the screw slot 36. The first 18a and second 18b stops can abut and interference fit against the lock screw 26 shaft when the outer cylinder 32 and inner cylinder 24 are rotated with respect to each other to the respective limits of rotation. The angular limit of rotation of the outer cylinder 32 with respect to the inner cylinder 24 can be defined by and identical to the screw slot angle. The screw slot angle can be an angle measured from the longitudinal axis 30 between the first stop 18a and the second stop 18b.

As described below in more detail in FIGS. 2A-2F and 3A-3B, spring device 50 can be used to capture and provide a semi-permanent locking of the outer cylinder 32 and inner cylinder 24 with respect to the first end piece 12a and second end piece 12b. Further, spring device 50 can be used to retain screw 26 and prevent the backing out of screw 26.

The outer cylinder 32 can have columns of radially inwardly-facing outer cylinder teeth 34. The outer cylinder teeth 34 can be configured in longitudinal columns parallel with the longitudinal axis 30. The outer cylinder teeth 34 can be oriented in transverse planes, perpendicular to the longitudinal axis 30 and along an angular path at a constant radius with respect to the longitudinal axis 30. The outer cylinder teeth 34 can be spaced so the toothless areas of the inner surface of the outer cylinder 32 can define a locking gap 28 between adjacent columns of outer cylinder teeth 34. The locking gaps 28 can be at least as wide as the width of the end piece teeth. The end piece teeth can be narrower than the outer cylinder teeth 34.

The end piece teeth can slide between the outer cylinder teeth 34 when the outer cylinder 32 is rotated appropriately with respect to the end pieces. When the guide pegs 20 are engaged in the guide slots 22, the end pieces and inner cylinder 24 can rotate as a single unit with respect to the outer cylinder 32. The screw slot 36 and screw can be configured so that the end piece teeth do not longitudinally interfere with the outer cylinder teeth 34 (i.e., an unlocked configuration) when the screw is at one end of the screw slot 36. For example, this unlocked configuration can permit the end pieces to longitudinally translate (i.e., expand and contract) with respect to the outer cylinder 32 and the opposite end piece.

The screw slot 36 and screw 26 can be configured so that the end piece teeth longitudinally interfere with the outer cylinder teeth 34 (i.e., a locked configuration) when the screw is at the opposite end of the screw slot 36 from the unlocked configuration. For example, this locked configuration can create an interference fit between the end piece teeth and the outer cylinder teeth 34, for example, substantially preventing the end pieces from longitudinally translating (i.e., expand and contract) with respect to the outer cylinder 32 and the opposite end piece.

The outer cylinder 32 can have a lock screw 26, such as a hex screw. The lock screw 26 can traverse the wall of the outer cylinder 32. The lock screw 26 can be configured to be radially translatable with respect to the outer cylinder 32 when screwed through the outer cylinder 32 wall. The lock screw 26 can be screwed toward the longitudinal center of the outer cylinder 32 to fix the outer cylinder 32 to the first end piece 12a, second end piece 12b, inner cylinder 24 or combinations thereof, for example, for additional locking.

Lock screw 26 can be tightened (e.g., screwed toward the center of the outer cylinder 32) to press the lock screw 26 against the first 12a and/or second 12b end piece and/or inner cylinder 24 to produce a frictional resistance. The lock screw 26 can deform the first end piece 12a and/or second end piece 12b, pressing the first 12a and/or second 12b end pieces (e.g., the respective extensions) into the inner cylinder 24, creating a frictional force between the inner cylinder 24 and the first 12a and/or second 12b end pieces 12b.

Lock screw 26 can be unscrewed away from the longitudinal center of the outer cylinder 32, releasing the first end piece 12a and second end piece 12b from being fixed to the outer cylinder 32. The first end piece 12a and/or second end piece 12b can be longitudinally translated or extended away from the outer cylinder 32. The guide pegs 20 can slide within the guide slots 22, restricting the end pieces from rotating with respect to the inner cylinder 24.

The device 4 can have snaps or threads on the end pieces, for example to engage the vertebral body 66 end plates. The end pieces can be smooth or rough (e.g., with texturing or teeth). The end pieces can have angles relative to the longitudinal axis 30 of the cylinders and/or the other end piece. The devices end pieces can have teeth or angle without the snap on pieces.

The end pieces can have four extensions, as shown, or more or less extensions. The end piece teeth can be next to each other, as shown, or can be in the center of each column. The ratio of the outer surface area of the end piece extensions covered by teeth to non-tooth surface area can be about 50%.

Figures 2A, 2B, 2C:
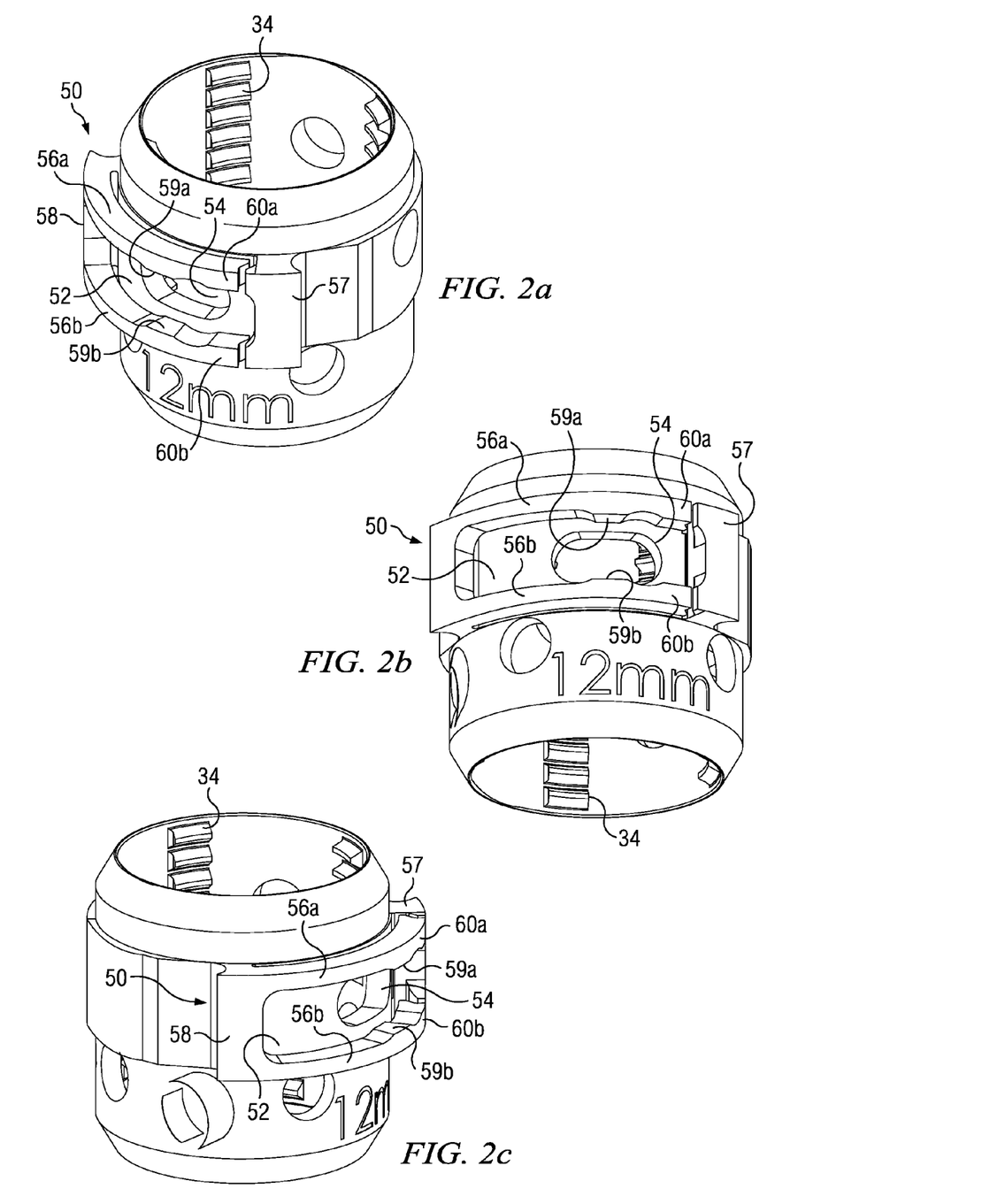
FIG. 2A is a perspective view of a spring device according to one embodiment of the present disclosure.
FIG. 2B is a perspective view of a spring device according to one embodiment of the present disclosure.
FIG. 2C is a perspective view of a spring device according to one embodiment of the present disclosure.
Figure 2D:
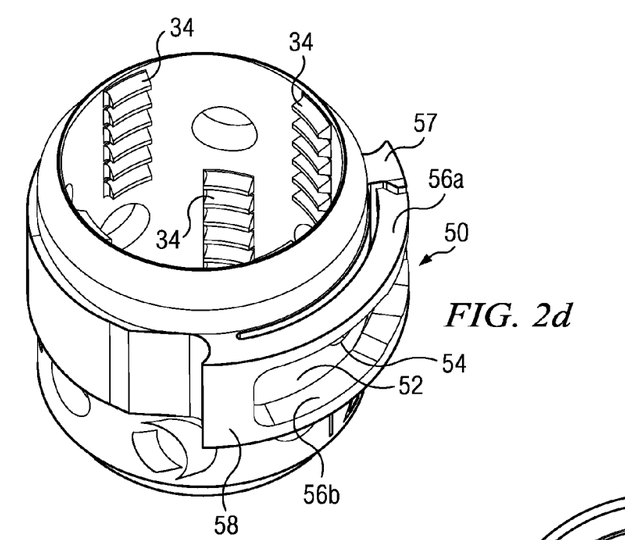
FIG. 2D is a perspective view of a spring device according to one embodiment of the present disclosure.

FIG. 2A is a perspective view of a spring device 50 according to one embodiment of the present disclosure. Spring device 50 may include a first spring arm 56a, a second spring arm 56b, and an end portion 58. Spring device 50 may include a middle notch 59a integral to first spring arm and a middle notch 59b integral to second spring arm, which may form two different apertures between spring arms 56a, 56b—an unlocked position 52 and a locked position 54. Spring device 50 may include an end notch 60a integral to the end of first spring arm 56a and an end notch 60b integral to the end of second of second spring arm 56b, such that end notches 60a, 60b may further define locked position 54. Spring device 50 may also include a stopping member 57.

In some embodiments, spring device 50 may be integral to outer cylinder 32 of an extendable vertebral body device 4. Accordingly, spring device 50 may be machined directly onto device 4, such that no separate pieces are attached to device 4. The machining process may be accomplished through any combination of machining operations, including, but not limited to, wire EDM, milling, turning, etc. For example, a heated wire having a very small diameter (e.g., twelve thousandth of an inch) may move radially along outer cylinder 32 to form the shape of spring device 50, including the small space formed between spring arms 56a, 56b and the outer cylinder 32. In another example, computer numerical control ("CNC") milling may be used to create the pocket between spring arms 56a, 56b, and to define middle notches 59a, 59b and end notches 60a, 60b of spring arms 56a, 56b.

In alternative embodiments, spring device 50 may be attached to a device in any suitable manner, including, but not limited to welding, fastening, clipping, using adhesives, etc.

In operation, spring device 50 may be used for positioning two components relative to one another and providing semi-permanent locking of the mated components (e.g., outer cylinder 32 mated with extension legs 12a,12b), which is described in more detail below in FIGS. 3A and 3B. As illustrated in FIG. 1, screw slot 36 on outer cylinder 32 may include a first stop 18a at a first terminal end of the screw slot 36, and a second stop 18b at a second terminal end of the screw slot 36. Accordingly, first stop 18a and second stop 18b may create a range of positions that screw 26 may be positioned, which may determine the range that outer cylinder 32 may be rotated about extendable legs 12a, 12b.

Unlocked position 52, which may be defined by end portion 58, spring arm 56a, middle notch 59a, spring arm 56b, and middle notch 59b, may create a first distinct position (or a range of distinct positions) of screw 26. This position is typically referred to as an unlocked position 52 because the outer cylinder teeth 34 may not be aligned with end piece teeth 16a, 16b, and thus the extendable legs 12a, 12b are unlocked to expand or contract.

Locked position 54, which may be defined by spring arm 56a, middle notch 59a, end notch 60a, spring arm 56b, middle notch 59b, and end notch 60b, may create a second distinct position of screw 26. This position is typically referred to as a locked position 54 because the outer cylinder teeth 34 may be aligned with end piece teeth 16a, 16b, and thus the extendable legs 12a, 12b are locked into that particular configuration.

Accordingly, unlocked position 52 and locked position 54 may be obtained by rotating the outer cylinder 32, such that screw 26 is engaged into one of these distinct positions of spring device 50.

In operation, spring device 50 may be used to effectively capture screw 26. Spring arms 56a, 56b may be flexible with a spring rate that can be adjusted accordingly. Middle notches 59a, 59b and end notches 60a, 60b of spring arms 56a, 56b may be designed in any suitable manner to effectively capture screw 26 in the locked position 54. For example, if a screw 26 with a cylindrical body and head is used, then middle notches 59a, 59b, end notches 60a, 60b, and/or spring arms 56a, 56b may be shaped appropriately to create a geometric shape to effectively capture this cylindrical shape. However, spring device 50 may be designed in any suitable manner to create a locked position 54 to effectively capture screw 26 of any geometric shape. In certain embodiments, locked position 54 of spring device 50 may cause friction with screw 26, such that the position of screw 26 is locked into place. The width between spring arms 56a, 56b may be dependent on the width of screw 26. Spring arms 56a, 56b may be of any suitable thickness and length to carry out the functions disclosed in this application. Generally, spring arms 56a, 56b may be thicker for greater strength or may be thinner for greater flexibility.

Figure 2E:
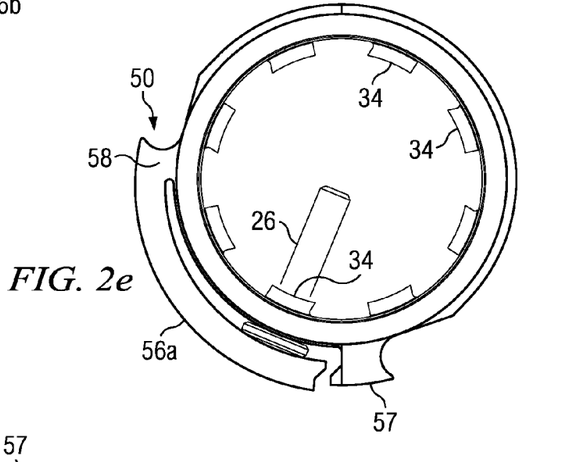
FIG. 2E is a top view of a spring device according to one embodiment of the present disclosure.
Figure 2F:
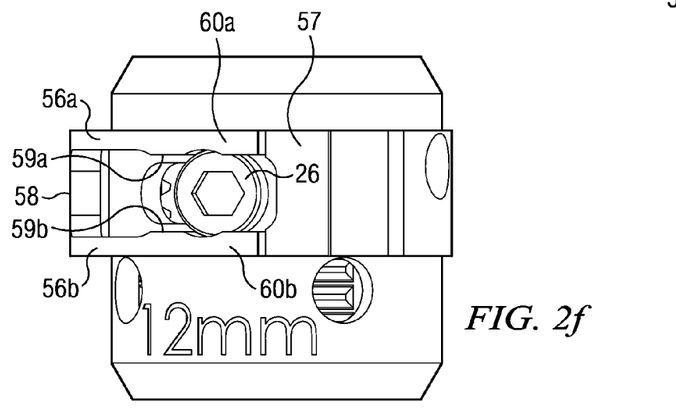
FIG. 2F is a perspective view of a spring device according to one embodiment of the present disclosure.

In operation, spring device 50 may also be used to prevent screw 26 from backing out. After screw 26 is located in locked position 54, the head of screw 26 may be driven into spring device 50, such that spring arms 56a, 56b naturally flex outward when an inward force is applied to screw 26. Accordingly, spring arms 56a, 56b allow passage of the head of screw 26 by flexing outward, and spring arms 56a, 56b may return to their unflexed position once the head of screw 26 has passed through spring arms 56a, 56b. After the head of screw 26 has completed passage through spring arms 56a, 56b, spring arms 56a, 56b may collapse to their natural unflexed position. Accordingly, spring device 50 acts as a retention mechanism to prevent screw 26 from backing out. As illustrated in FIG. 2E, the head of the screw 26 may rest within the pocket formed between spring device 50 and outer cylinder 32. As illustrated in FIG. 2E, the natural, unflexed position of spring arms 56a, 56b may cover the top of the head of screw 26, which prevents screw 26 from backing out.

In some embodiments, middle notches 59a, 59b and/or end notches 60a, 60b may engage with a notched feature on screw 26 to prevent rotation of screw 26, which may prevent screw 26 from backing out. In some embodiments, screw 26 may be a cotter pin 26, such that the end notches 60a, 60b engage the head of the cotter pin 26, which prevents screw 26 from backing out. In some embodiments, the design of the body of screw 26 may include a portion with an enlarged diameter, such that the enlarged diameter may cause the spring arms 56a, 56b to flex outwardly when force is applied, such that this enlarged diameter of the body of screw 26 may become retained by spring arms 56a, 56b, which prevents screw 26 from backing out even if the head of screw 26 sits above spring arms 56a, 56b. Any suitable design of screw 26 interacting with an equally suited design of spring device 50 may be used to retain screw 26 which prevents screw 26 from backing out. Accordingly, spring device 50 prevents screw 26 from backing out even if spring device 50, device 4, or screw 26 would typically become loosened after being subject to shock, vibration, or any other type of disturbance.

In some embodiments, screw 26 may be inserted directly into the locked position 54 until the screw is properly retained by spring arms 56a, 56b such that screw 26 cannot be inadvertently backed out of spring device 50.

In some embodiments, first spring arm 56a and second spring arm 56b are generally parallel to one another in an unflexed position, and are generally perpendicular to end portion 58. In alternative embodiments, spring arms 56a, 56b may be configured in any shape and do not necessarily have to be parallel to one another to achieve the teachings in the disclosure.

FIGS. 2B, 2C, 2D, 2E, and 2F illustrate different perspective views of a spring device 50 integral with an outer cylinder 32 of an extendable vertebral body replacement 4 according to one embodiment of the present disclosure.

Although FIGS. 2A-2F illustrate spring device 50 integral to a cylinder 32 of an extendable vertebral body device 4, spring device 50 may be integral to any geometrical shape of any type of device, including, but not limited to expandable support devices with only one extension leg, an interbody device having a flat surface, a cover plate, a cervical plate, an implant system, etc.

Figure 3A:
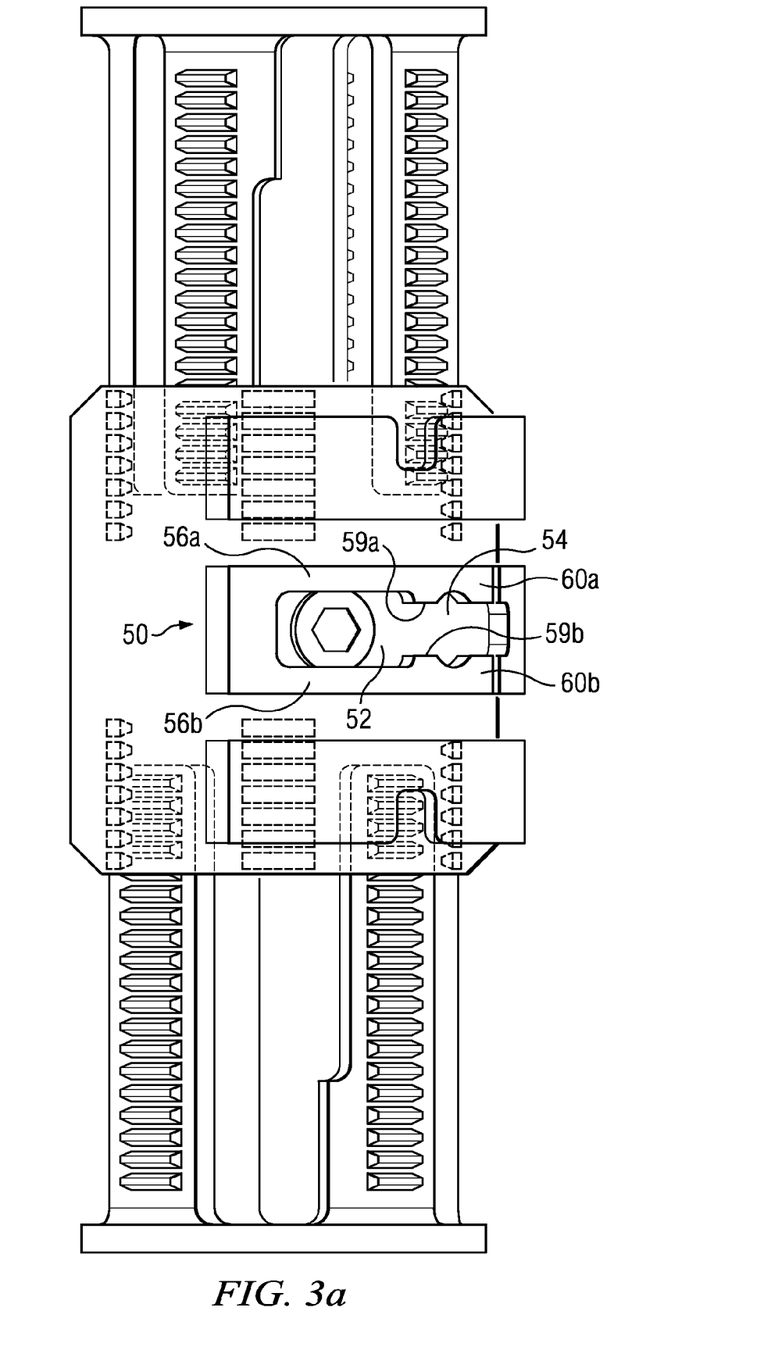
FIG. 3A is a partially see-through view of an expandable support device in a longitudinally expanded configuration with a screw in the unlocked configuration of a spring device according to one embodiment of the present disclosure.

FIG. 3A is a partially see-through view of an expandable support device 4 in a longitudinally expanded configuration with a screw 26 in the unlocked configuration of a spring device 50 according to one embodiment of the present disclosure. In the unlocked configuration, first end piece 12a and second end piece 12b can be expanded and/or contracted to the desired position.

Figure 3B:
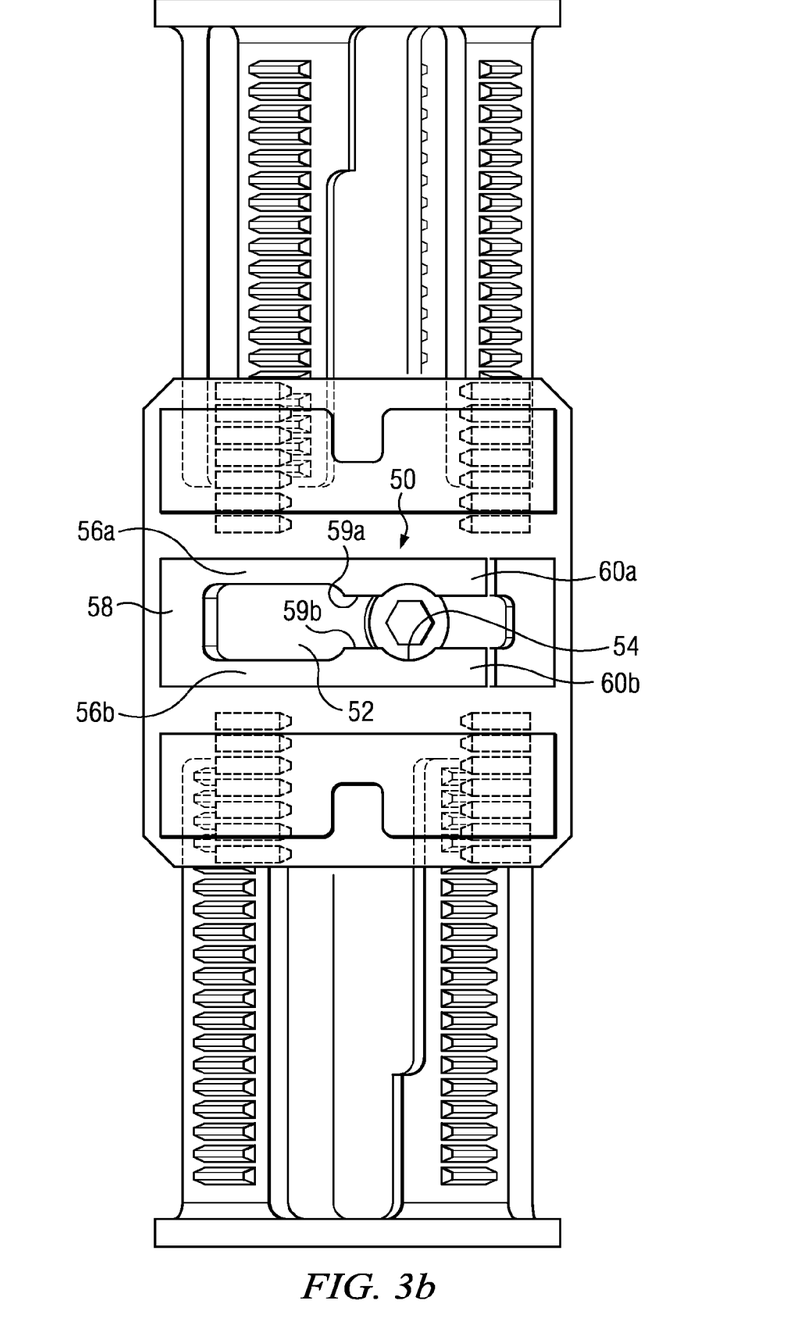
FIG. 3B is a partially see-through view of an expandable support device in a longitudinally expanded configuration with a screw in the locked configuration of a spring device according to one embodiment of the present disclosure.

FIG. 3B is a partially see-through view of an expandable support device 4 in a longitudinally expanded configuration with a screw 26 in the locked configuration of a spring device 50 according to one embodiment of the present disclosure. When a force is applied to outer cylinder 32 to rotate the device into a locked configuration, the rotational force applied to outer cylinder 32 will also cause screw 26 positioned in unlocked position 52 to apply force to middle notches 59a, 59b of spring device 50, which can cause spring arms 56a, 56b to flex outwardly and allow passage of screw 26 into locked position 54. After screw has moved past middle notches 59a, 59b into the locked position 54, spring arms 56a, 56b may return to their natural unflexed positions. End notches 60a, 60b may prevent screw 26 from rotating too far, if screw slot 36 has not already prevented screw 26 from further rotation. Additionally, stopping member 57, as illustrated in FIGS. 2A-2F may also prevent screw 26 from moving outside of spring arms 56a, 56b.

After screw 26 has been rotated into the locked position 54, an inward force may be applied to screw 26. Accordingly, spring arms 56a, 56b may flex outward to allow passage of the head of screw 26, and spring arms 56a, 56b may return to their unflexed position once the head of screw 26 has passed through spring arms 56a, 56b. After the head of screw 26 has been forced through spring arms 56a, 56b, spring arms 56a, 56b may collapse to their natural unflexed position, such that a retention mechanism is established which prevents screw 26 from inadvertently backing out.

Screw 26 can be unscrewed, such that the force of removing screw 26 causes spring arms 56a, 56b to flex outwardly. After backing out screw 26, outer cylinder 32 may be rotated back to the unlocked configuration, which allows device 4 to be compressed, expanded, repositioned, and/or removed from the target site.

FIG. 4A is a lateral view of an expandable support device 44 in its compressed configuration within vertebral bodies of a spine 62 according to one embodiment of the present disclosure. FIG. 4A illustrates spine 62 with one or more adjacent intervertebral discs 60 removed. Expandable support device 44 can be in a longitudinally compressed configuration. The expandable support device 44 can be inserted into the target site in the longitudinally compressed configuration or in a longitudinally expanded configuration (e.g., by wedging the expandable support device 44 into the target site and compressing the expandable support device 44 between the remaining vertebral bodies 66 adjacent the target site during insertion). The device longitudinal axis 70 of the expandable support device 44 can be substantially parallel with the spinal longitudinal axis 72. The device can be implanted in the spine 62 for partial or complete corpectomy.

FIG. 4B is a lateral view of an expandable support device 44 in its extracted and locked configuration within vertebral bodies of a spine 62 according to one embodiment of the present disclosure. FIG. 4B illustrates that the expandable support device 44 can be longitudinally expanded 48 in the target site. During expansion, the outer cylinder 32 can be in a rotated position with respect to the inner cylinder 24 and the first 12a and second 12b end pieces so the first 16a and second 16b end piece teeth are aligned into the locking gap 28 and slide unobstructed through the outer cylinder 32, in turn allowing the first 12a and second 12b end pieces to slide longitudinally away from the inner 24 and outer 32 cylinders.

The guide pegs 20 can slide longitudinally along the guide slots 22. The guide slots 22 can prevent the guide pegs 20 and the first 12a and second 12b end pieces from rotating with respect to the inner cylinder 24. The guide slots 22 can interference fit when the guide pegs 20 reach the extent of the guide slots 22. The guide slots 22 can limit longitudinal travel of the guide pegs 20, preventing the first 12*a* and second 12*b* end pieces from separating from the inner 24 and/or outer 32 cylinders.

When the device is expanded, the device first end 8*a* and the device second end 8*b* can be in contact the respective vertebral bodies 66 adjacent to the target site between vertebral bodies. The first 10*a* and second 10*b* end faces can be in surface contact with the vertebral bodies 66 or dig or sink into the vertebra 64, for example compressing or diverting some cortical bone. For example, anchors on the first 10*a* and/or second 10*b* end faces can be sharp and protrude into the vertebrae 64. The first 10*a* and/or second 10*b* end faces can have an ingrowth matrix, anchoring the device 44 to new bone growth through the ingrowth matrix after deployment of the device 44.

The outer cylinder 32 can be rotated, with respect to the inner cylinder 24 and end pieces, transforming the device into a locked configuration. The rotated outer cylinder 32 can lock the device in a longitudinally expanded configuration with spring device 50, such that screw 26 cannot be inadvertently backed out or loosened, as described above in FIGS. 3A and 3B. For example, in the locked configuration, the outer cylinder teeth 34 can form an interference fit with the first end piece teeth 16*a* and the second end piece teeth 16*b*. The rotation of the outer cylinder 32 shown in FIG. 4B can be reversed to unlock the device, for example for repositioning or removal.

The device 44 can be partially or substantially completely filled with a filler through the slots between the end piece extensions and/or through the ports formed at the longitudinal ends of the device 44. The device 44 can be filled by the filler before and/or after deployment into the target site between vertebral bodies.

A physician can adjust the length of the device 44 after inspecting the target site between vertebral bodies. More than one device 44 can be placed longitudinal end-to-end with other devices 44, for example to stack the devices as desired.

The expandable support device 44 can be deployed in a vessel, in or around an aneurysm, across a valve, or combinations thereof. The expandable support device 44 can be deployed permanently and/or used as a removable tool to expand or clear a lumen and/or repair valve leaflets.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

If spring device 50 is machined onto device 44, the material must be made of a material that can conduct electricity. Otherwise, any or all elements of the expandable support devices 44, and/or deployment tool, and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable support devices 44, and/or deployment tool, and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), poly ester amide (PEA), polypropylene, PTFE, ePTFE, nylon, extruded collagen, silicone, any other material disclosed herein, or combinations thereof.

The expandable support devices 44 and/or deployment tool, and/or elements of the expandable support devices 44, and/or deployment tool, and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin E.sub.2 Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A locking device for locking an expandable support device, the locking device comprising:
    a spring device integral with the expandable support device, wherein the spring device comprises an end portion, a first flexible arm, and a second flexible arm, and wherein the expandable support device comprises:
        a first member having an outer cylinder, wherein the outer cylinder comprises a slot;
        a second member positioned radially inside of the first member, the second member configured to rotate with respect to the first member, and wherein the second member comprises a hole; and
        a fastener extending through the spring device, the slot of the first member, and the hole of the second member, wherein the fastener comprises a head; and
    wherein a first aperture of the spring device is adapted to position the fastener associated with a first rotational position and wherein a second aperture of the spring device is adapted to position the fastener associated with a second rotational position, and wherein the first flexible arm and the second flexible arm are adapted to flex outward and allow passage of the fastener head when an inward pressure is applied to the fastener positioned in the second aperture, and wherein the first flexible arm and the second flexible arm are adapted to collapse to their unflexed position after the fastener head has completed passage through the spring device, wherein the first flexible arm and the second flexible arm are adapted to cover the fastener head and prevent the fastener from backing out.

2. The locking device of claim 1, wherein the expandable support device further comprises a longitudinally extending member configured to longitudinally slide with respect to the first member in a first direction away from the first member when the first member is in the first rotational position with respect to the longitudinally extending member, and wherein a second direction away from the first member is opposite to the first direction away from the first member, and wherein the longitudinally extending member is configured to be longitudinally fixed with respect to the first member when the first member is in the second rotational position with respect to the longitudinally extending member.

3. The locking device of claim 1, wherein the first aperture and second aperture of the spring device are smaller regions in a greater aperture of the spring device.

4. The locking device of claim 1, wherein the first aperture of the spring device is defined by the end portion, a portion of the first flexible arm, a notch positioned on the first flexible arm, a portion of the second flexible arm, and a notch positioned on the second flexible arm.

5. The locking device of claim 1, wherein the second aperture of the spring device is defined by a portion of the first flexible arm, a notch positioned on the first flexible arm, an end notch positioned at the end of the first flexible arm, a portion of the second flexible arm, a notch positioned on the second flexible arm, and an end notch positioned at the end of the second flexible arm.

6. The locking device of claim 1, wherein the second aperture of the spring device is configured to tightly capture the fastener.

7. The locking device of claim 1, wherein the fastener head can be seated within a gap formed between the first and second arms with the first member.

8. The locking device of claim 1, wherein the fastener is a screw.

9. The locking device of claim 1, wherein the spring device is machined onto the expandable support device.

10. The locking device of claim 1, wherein the flexible arms are oriented in a plane perpendicular to the longitudinal axis.

11. An extendable support device having a longitudinal axis comprising:
    a first member having an outer cylinder, wherein the outer cylinder comprises a slot and a spring device;
    a second member positioned radially inside of the first member, the second member configured to rotate with respect to the first member, and wherein the second member comprises a hole;
    a fastener extending through the spring device, the slot of the first member, and the hole of the second member, wherein the fastener comprises a head; and
    wherein the spring device comprises an end portion, a first flexible arm, and a second flexible arm, wherein the end portion is integral with the first member, wherein the first arm and second arm are separated from the first member by a gap, wherein a first aperture of the spring device is adapted to position the fastener associated with a first rotational position and a second aperture of the spring device is adapted to position the fastener associated with a second rotational position, and wherein the first flexible arm and the second flexible arm are adapted to flex outward and allow passage of the fastener head when an inward pressure is applied to the fastener positioned in the second aperture, and wherein the first flexible arm and the second flexible arm are adapted to collapse to their unflexed position after the fastener head has completed passage through the spring device, wherein the first flexible arm and the second flexible arm are adapted to cover the fastener head and prevent the fastener from backing out.

12. The extendable supportable device of claim 11, further comprising a longitudinally extending member configured to longitudinally slide with respect to the first member in a first direction away from the first member when the first member is in the first rotational position with respect to the longitudinally extending member, and wherein a second direction away from the first member is opposite to the first direction away from the first member, and wherein the longitudinally extending member is configured to be longitudinally fixed with respect to the first member when the first member is in the second rotational position with respect to the longitudinally extending member.

13. The extendable supportable device of claim 11, wherein the first aperture and second aperture of the spring device are smaller regions in a greater aperture of the spring device.

14. The extendable supportable device of claim 11, wherein the first aperture of the spring device is defined by the end portion, a portion of the first flexible arm, a notch positioned on the first flexible arm, a portion of the second flexible arm, and a notch positioned on the second flexible arm.

15. The extendable supportable device of claim 11, wherein the second aperture of the spring device is defined by a portion of the first flexible arm, a notch positioned on the first flexible arm, an end notch positioned at the end of the first flexible arm, a portion of the second flexible arm, a notch positioned on the second flexible arm, and an end notch positioned at the end of the second flexible arm.

16. The extendable supportable device of claim 11, wherein the second aperture of the spring device is configured to tightly capture the fastener.

17. The extendable supportable device of claim 11, wherein the fastener head can be seated within the gap formed between the first and second arms with the first member.

18. The extendable supportable device of claim 11, wherein the fastener is a screw.

19. The extendable supportable device of claim 11, wherein the spring device is machined onto the expandable support device.

20. The extendable supportable device of claim 11, wherein the flexible arms are oriented in a plane perpendicular to the longitudinal axis.

* * * * *